(12) United States Patent
Hopkins (10) Patent No.: US 9,968,699 B2
(45) Date of Patent: May 15, 2018

(54) FRAGRANCE ENHANCER

(71) Applicant: Jeffrey Hopkins, Columbia Station, OH (US)

(72) Inventor: Jeffrey Hopkins, Columbia Station, OH (US)

(*) Notice: Subject to any disclaimer, the term of this patent is extended or adjusted under 35 U.S.C. 154(b) by 206 days.

(21) Appl. No.: 14/918,285

(22) Filed: Oct. 20, 2015

(65) Prior Publication Data

US 2016/0038623 A1    Feb. 11, 2016

Related U.S. Application Data

(63) Continuation-in-part of application No. 14/163,409, filed on Jan. 24, 2014, now abandoned.

(60) Provisional application No. 61/757,906, filed on Jan. 29, 2013.

(51) Int. Cl.
*A61L 9/03* (2006.01)
*F21V 35/00* (2006.01)

(52) U.S. Cl.
CPC ..................................... *A61L 9/03* (2013.01)

(58) Field of Classification Search
CPC .................................. A61L 9/03; A61L 9/032
USPC ........................................................... 422/124
See application file for complete search history.

(56) References Cited

U.S. PATENT DOCUMENTS

| | | | |
|---|---|---|---|
| 6,783,356 B2 | 8/2004 | Hermanson | |
| 8,240,082 B1* | 8/2012 | Fall | A01M 1/08 43/113 |
| 2004/0003724 A1 | 1/2004 | Ellis | |
| 2014/0334801 A1* | 11/2014 | Browder | A61L 9/03 392/390 |
| 2015/0130089 A1* | 5/2015 | Westphal | A61L 9/122 261/30 |

* cited by examiner

*Primary Examiner* — Kevin Joyner
*Assistant Examiner* — Holly M Mull
(74) *Attorney, Agent, or Firm* — McDonald Hopkins LLC (57) ABSTRACT

The present invention relates to fragrance enhancers for use in conjunction with candles to enhance the dispersion of the fragrance therefrom and/or increase the combustion efficiency thereof. In one embodiment, the fragrance enhancer of the present invention comprises a body that is mounted to an upper surface of the holder and further comprises a mounting bracket for holding a fan assembly that is mounted to the holder. In one instance, the fan assembly includes a plurality of inverted blades, and a gap is formed between the body and the holder to enable air flow through the body. In another embodiment the fragrance enhancer of the present invention comprises a cylindrically-shaped perforated body, the cylindrically-shaped perforated body having openings located at both the top and bottom thereof. In this embodiment the fragrance enhancer of the present invention further comprises a fan assembly formed from inclined blades.

20 Claims, 9 Drawing Sheets

FRAGRANCE ENHANCER

RELATED APPLICATION DATA

This application claims priority to and is a continuation-in-part of U.S. patent application Ser. No. 14/163,409 filed Jan. 24, 2014 and entitled "Fragrance Enhancer," which claims priority to U.S. Provisional Patent Application No. 61/757,906 filed Jan. 29, 2013 and entitled "Fragrance Enhancer," the disclosures of which are hereby incorporated by reference herein in their entireties.

FIELD OF THE INVENTION

The present invention relates to fragrance enhancers for use in conjunction with candles to enhance the dispersion of the fragrance therefrom and/or increase the combustion efficiency thereof. In one embodiment, the fragrance enhancer of the present invention comprises a body that is mounted to an upper surface of the holder and further comprises a mounting bracket for holding a fan assembly that is mounted to the holder. In one instance, the fan assembly includes a plurality of inverted blades, and a gap is formed between the body and the holder to enable air flow through the body. In another embodiment the fragrance enhancer of the present invention comprises a cylindrically-shaped perforated body, the cylindrically-shaped perforated body having openings located at both the top and bottom thereof. In this embodiment the fragrance enhancer of the present invention further comprises a fan assembly formed from inclined blades.

BACKGROUND OF THE INVENTION

The present disclosure relates to candles. More particularly, it relates to an apparatus for increasing the airflow from a lighted candle for faster circulation of the fragrance emitted from the candle and/or a more efficient combustion of the candle.

Existing candles are often formed and sold within glass jars. While the candles often emit strong or aromatic fragrances when lit, the dispersement of the fragrance may be inhibited by a lack of airflow or the location of the candle in the room.

Thus, there is a need for an apparatus which improves the airflow and dispersement of a fragrance emitted from a candle and/or improves the combustion efficiency of a candle.

SUMMARY OF THE INVENTION

The present invention relates to fragrance enhancers for use in conjunction with candles to enhance the dispersion of the fragrance therefrom and/or increase the combustion efficiency thereof. In one embodiment, the fragrance enhancer of the present invention comprises a body that is mounted to an upper surface of the holder and further comprises a mounting bracket for holding a fan assembly that is mounted to the holder. In one instance, the fan assembly includes a plurality of inverted blades, and a gap is formed between the body and the holder to enable air flow through the body. In another embodiment the fragrance enhancer of the present invention comprises a cylindrically-shaped perforated body, the cylindrically-shaped perforated body having openings located at both the top and bottom thereof. In this embodiment the fragrance enhancer of the present invention further comprises a fan assembly formed from inclined blades.

In accordance with one aspect of the disclosure, a fragrance enhancer for a candle has a body which is configured to be mounted on an upper surface of a candle holder; a mounting bracket positioned at an upper end of the body; a fan assembly rotatably mounted to the mounting bracket; and the fan assembly has a plurality of inverted blades which disperse fragrance from the candle.

In accordance with another aspect of the disclosure, a fragrance enhancer and candle assembly has a candle and a holder for housing a candle; a body mounted to an upper surface of the holder; a mounting bracket for holding a fan assembly; wherein the fan assembly has a plurality of inverted blades; and a gap is formed between the body and the holder to enable air flow through the body.

Another aspect of the disclosure is an apparatus which is removably attached to an upper portion of a candle jar. Yet another aspect of the disclosure is an apparatus which fits onto a conventional 14.5 ounce candle jar. Another aspect of the disclosure is a fragrance enhancer which is made of aluminum to minimize the enhancer becoming overheated. Still another aspect of the disclosure is air inlet holes in the apparatus to allow air into the candle to maintain a lit flame. Yet another aspect of the disclosure is air inlet holes with different ornamental configurations. Still another aspect of the disclosure is an inverted fan blade for more efficient airflow. Another aspect of the disclosure is a series of angled blades which rotate and dispense scent from the candle.

In accordance with still another aspect of the disclosure, a fragrance enhancer for a candle comprises: a top cylindrically-shaped ring, wherein the top cylindrically-shaped ring has a cylindrical channel formed therein; a bottom cylindrically-shaped ring, wherein the bottom cylindrically-shaped ring has a cylindrical channel formed therein; a cylindrically-shaped perforated screen, where the cylindrically-shaped perforated screen is designed to operatively engage both of the cylindrical channels located in the top and bottom cylindrically-shaped rings; a fan assembly support bracket formed so as to have a plurality of fan assembly support bracket arms, each fan assembly support bracket arm having a tooth formed at the end thereof so as to operatively engage at least one perforation in the cylindrically-shaped perforated screen; a fan assembly formed from a plurality of inverted inclined fan blades, wherein the fan assembly support bracket and the fan assembly are operatively coupled so that the fan spins in response to rising heat and/or convection currents.

In accordance with still another aspect of the disclosure, a fragrance enhancer for a candle comprises: a top cylindrically-shaped ring, wherein the top cylindrically-shaped ring has a cylindrical channel formed therein; a bottom cylindrically-shaped ring, wherein the bottom cylindrically-shaped ring has a cylindrical channel formed therein; a cylindrically-shaped perforated screen, where the cylindrically-shaped perforated screen is designed to operatively engage both of the cylindrical channels located in the top and bottom cylindrically-shaped rings; a fan assembly support bracket formed so as to have a plurality of fan assembly support bracket arms, each fan assembly support bracket arm having a tooth formed at the end thereof so as to operatively engage at least one perforation in the cylindrically-shaped perforated screen; a fan assembly formed from a plurality of inverted inclined fan blades, wherein the fan assembly support bracket and the fan assembly are operatively coupled so that the fan spins in response to rising heat and/or convection currents, wherein the fan assembly support bracket and the fan assembly are operatively coupled by a pin and post combination.

Other aspects of the disclosure will become apparent upon a reading and understanding of the following detailed description.

DETAILED DESCRIPTION OF THE INVENTION

The present invention relates to fragrance enhancers for use in conjunction with candles to enhance the dispersion of the fragrance therefrom and/or increase the combustion efficiency thereof. In one embodiment, the fragrance enhancer of the present invention comprises a body that is mounted to an upper surface of the holder and further comprises a mounting bracket for holding a fan assembly that is mounted to the holder. In one instance, the fan assembly includes a plurality of inverted blades, and a gap is formed between the body and the holder to enable air flow through the body. In another embodiment the fragrance enhancer of the present invention comprises a cylindrically-shaped perforated body, the cylindrically-shaped perforated body having openings located at both the top and bottom thereof. In this embodiment the fragrance enhancer of the present invention further comprises a fan assembly formed from inclined blades.

As such, in general the present disclosure relates to candles and more to apparatuses for increasing the airflow to a lighted candle for faster circulation of the fragrance emitted therefrom and/or to increase the combustion efficiency thereof.

Referring now to FIGS. 1 through 4, a fragrance enhancer 10 in accordance with a first embodiment is shown. The fragrance enhancer 10 is formed preferably from aluminum so as to prevent overheating of the enhancer from a lit wick 11 of a candle 12. The enhancer may be formed in a cylinder, cone or tapered configuration and is inserted or mounted to an upper end of a candle jar 13. The enhancer is preferably sized to fit on a conventional 14.5 ounce candle jar, but other sizes are contemplated by the disclosure. A plurality of air inlet holes 14 are formed on side walls 16 of the cone or cylinder 17 to allow air to enter the candle so the flame from the candle is not snuffed out. In accordance with one aspect of the disclosure, the air inlet holes can be stamped in different ornamental configurations such as Christmas trees, pumpkins for Halloween, and flags and stars for 4th of July, etc.

Figure 1:
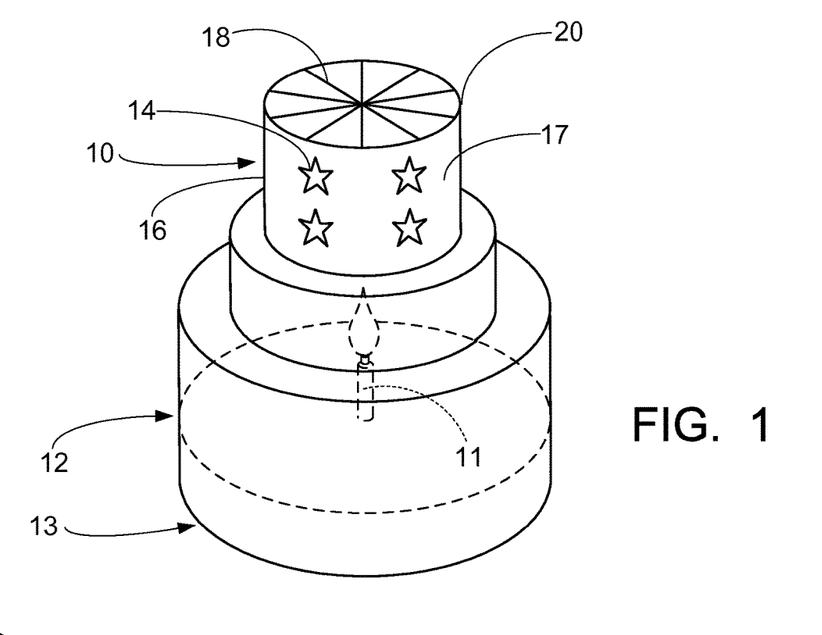
FIG. 1 is a perspective view of a candle jar with a fragrance enhancer in accordance with one embodiment of the disclosure.
Figure 2:
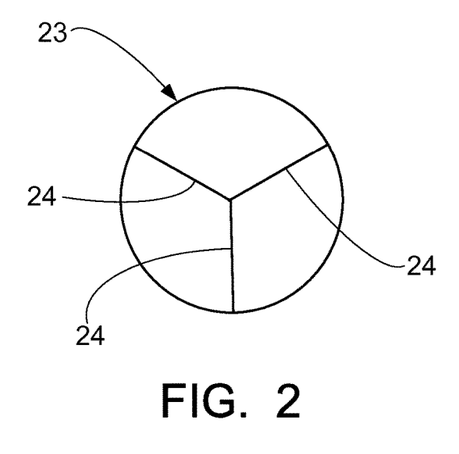
FIG. 2 is a top plan view of a fan mounting bracket of FIG. 1.
Figure 3:
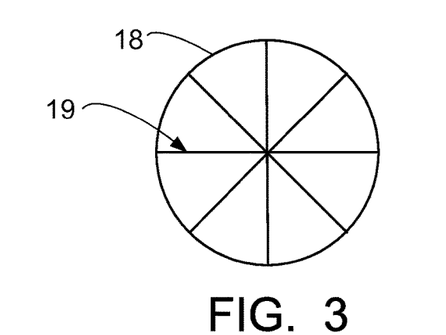
FIG. 3 is a top plan view of a fan of the fragrance enhancer of FIG. 1.
Figure 4:
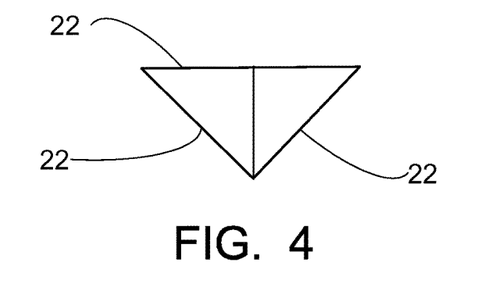
FIG. 4 is a side elevational view of the fan of FIG. 3.
Figure 5:
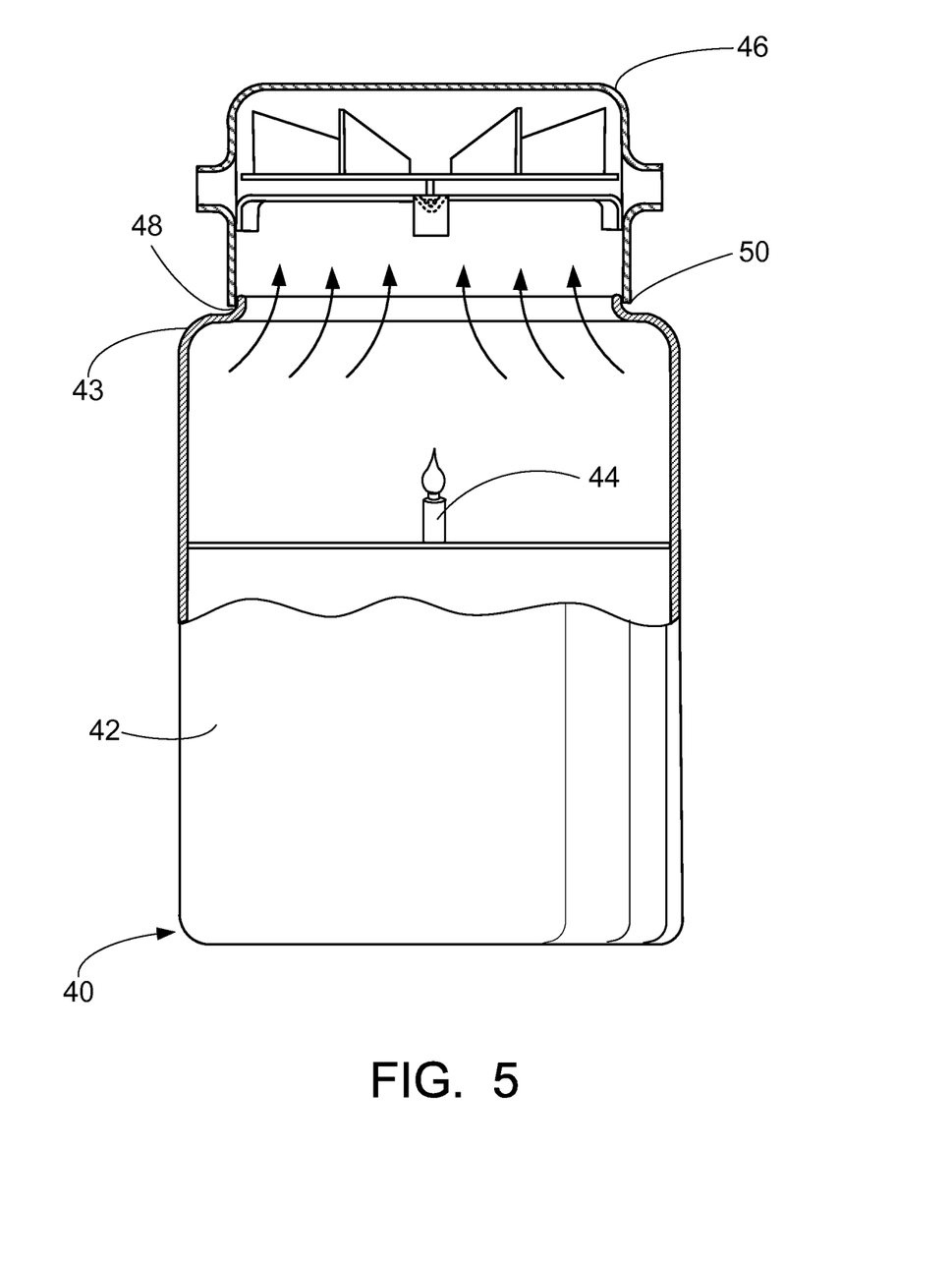
FIG. 5 is a side elevational view in cross-section of a fragrance enhancer in accordance with another embodiment of the present disclosure.
Figure 6A:
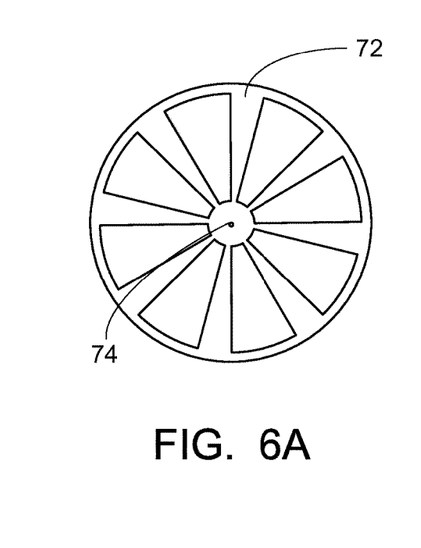
FIG. 6A is a top plan view of a dispensing fan in accordance with another aspect of the disclosure.
Figure 6B:
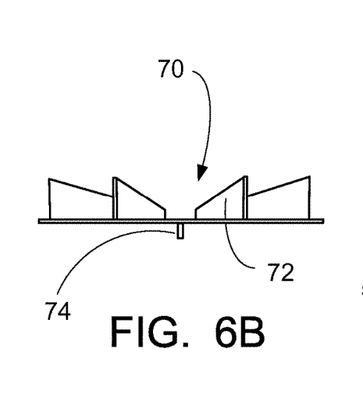
FIG. 6B is a side elevational view of the fan of FIG. 6A.
Figure 7A:
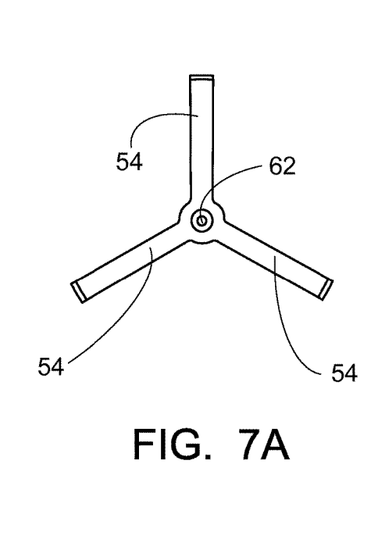
FIG. 7A is a top plan view of a fan mounting bracket in accordance with another aspect of the disclosure.
Figure 7B:
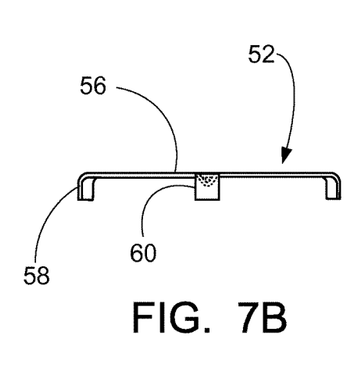
FIG. 7B is a side elevational view of the fan bracket of FIG. 7A.
Figure 8A:
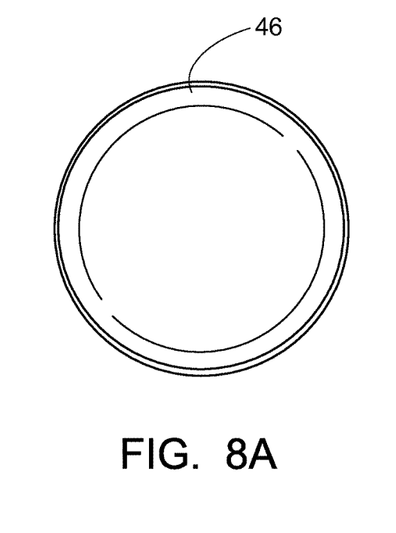
FIG. 8A is a top plan view of a lid in accordance with another aspect of the disclosure.
Figure 8B:
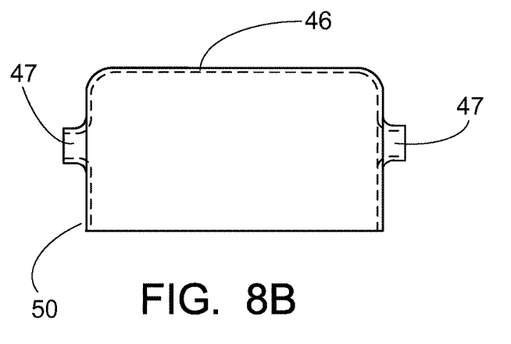
FIG. 8B is a side elevational view of the lid of FIG. 8A.

Referring now to FIG. 3, a fan 18 with a blade assembly 19 is provided at an upper end 20 of the cylinder 17. Referring to FIG. 4, the fan preferably has inverted blades 22 for more efficient operation and improved air flow. Referring to FIG. 2, a mounting bracket assembly 23 has three spaced apart brackets 24 (more of these brackets can also be used) which are used to rotatably hold the fan arrangement and are positioned below the fan. The brackets 24 are mounted at upper end 20 of the cone. Heat from the lit candle wick rises and results in rotation of the fan blade, which in turn disperses the fragrance at a higher rate to the atmosphere outside of the candle jar.

Referring now to FIGS. 5 through 8B, a fragrance enhancer 20 in accordance with another aspect of the disclosure is shown. A candle jar 40 has a candle 42 and wick 44 enclosed therein. A lid 46 is positioned on a top surface 43 of the candle jar. A space or gap 48 is formed near a bottom end 50 of the lid to allow cooler airflow to enter the lid. A fan assembly support bracket 52 has three spaced apart brackets 54 having a top member 56 and a downwardly bent edge 58 which retains the bracket within the lid. A center member 60 has a hole or opening 62 therein for holding an inverted blade assembly 70. Blade assembly 70 has a plurality of spaced apart inverted blades 72 which disperse air and the fragrance from the candle. A pin or post 74 is used to mount the fan assembly to the bracket post 60. The cooler air flows through gap 48 and, along with the heat from the candle wick which arises, causes the fan blades to rotate, thus dispersing the fragrance into the atmosphere and through inlet holes 47.

The foregoing non-limiting exemplary embodiment has been described with reference to the embodiment of FIGS. 1 through 8B embodiment. A motorized or mechanized fan assembly can also be used as part of the disclosure. Obviously, modifications and alterations of the various embodiments of FIGS. 1 through 8B will occur to others upon a reading and understanding of the preceding detailed description. It is intended that the exemplary non-limiting embodiments of FIGS. 1 through 8B be construed as including all such modifications and alterations insofar as they come within the scope of the above description or the equivalents thereof.

Turning to the embodiments of FIGS. 9A through 15, the present invention further relates to a fragrance enhancer 100 that comprises a fan assembly 102, where such a fan assembly 102 is formed from a plurality of inverted inclined blades 104 (although eight are shown any suitable number can be utilized); a top cylindrically-shaped ring 106; a bottom cylindrically-shaped ring 108; and a cylindrically-shaped perforated screen 110, where the top and bottom cylindrically-shaped rings 106 and 108 each have a channel (106a and 108a, respectively—see FIG. 10) sized to receive the top and bottom edges of screen 110. In one embodiment, both the top and bottom cylindrically-shaped rings 106 and 108 each respectively have an internal lip, or ledge, 112 and 114 formed thereon. In another embodiment, only bottom cylindrically-shaped ring 108 has an internal lip, or ledge, 114 formed thereon. In the case of bottom cylindrically-shaped ring 108 and its lip, or ledge, 114, these structures are formed to be any suitable size so as to fit snugly on the top lip 116 of a jar candle 118 (see FIG. 10—items shown in dashed lines). It should be noted that although bottom cylindrically-shaped ring 108 and its lip, or ledge, 114 are formed so as to snugly fit a typical jar candle top, the fit need not be air-tight. In another embodiment, bottom cylindrically-shaped ring 108 and its lip, or ledge, 114 can be formed so as to be any size regardless of whether or not such size fits over the top of a typical jar candle. In such a case a suitably formed adapter (not shown) can be used so as to enable fragrance enhancer 100 to fit any size candle. In fact such an adapter could be designed to permit the cylindrically-shaped fragrance enhancer 100 to fit other geometrically shaped candle jars including, but not limited to, square, diamond, polygonal, rectangular, etc. (see, e.g., FIGS. 9B and 9C). In one embodiment, such an adapter is formed from a round male end sized to snugly fit the internal diameter of bottom cylindrically-shaped ring 108 and to engage lip, or ledge, 114. The opposite end of such an adapter is then a female opening of any geometric shape designed to fit over the top of any desired jar candle. In one instance, both the male and female portions of such an adapter would be round.

As would be appreciated by those of skill in the art, the height of such an adapter is not critical so long as the height of same is not too high to cause instability in fragrance enhancer 100 when mounted onto such an adapter that has been placed on the top of a desired jar candle. In this manner fragrance enhancer 100 of the present invention can be made to essentially fit a wide variety of jar candle sizes and geometric types without having to change the overall design and size of fragrance enhancer 100. Essentially, this permits a one-size fits all scenario where fragrance enhancer 100 only needs to be manufactured in one size. Alternatively, as would be apparent to those of skill in the art, it may be desirable to manufacture fragrance enhancer in multiple different sizes so that a given sized device would specifically fit a specific type of candle jar. For example, so as to specifically manufacture a fragrance enhancer designed to natively fit a candle jar by the Yankee Candle Company.

Figures 9A, 9B, 9C:
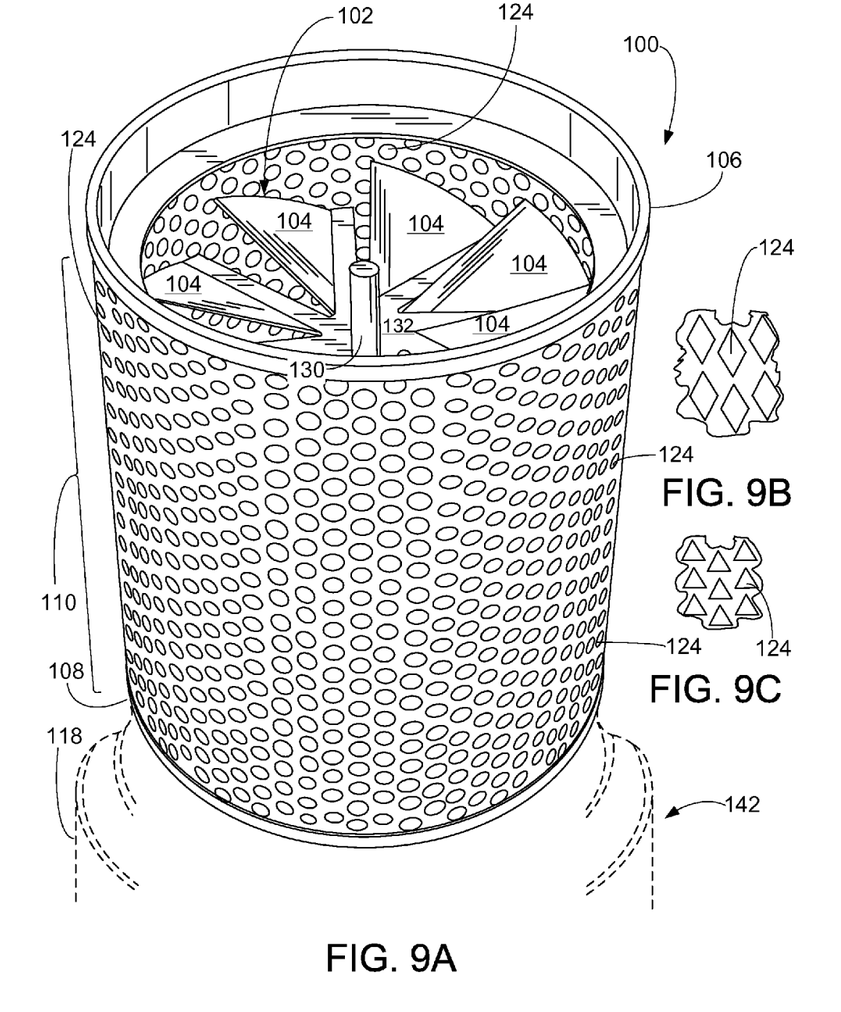
FIG. 9A is a side perspective view of a fragrance enhancer in accordance with another embodiment of the present invention with a top portion of a candle shown in dashed lines.
FIGS. 9B and 9C are close up illustrations of alternative embodiments for the openings in the cylindrical body of the fragrance enhancer of FIG. 9A.
Figure 11:
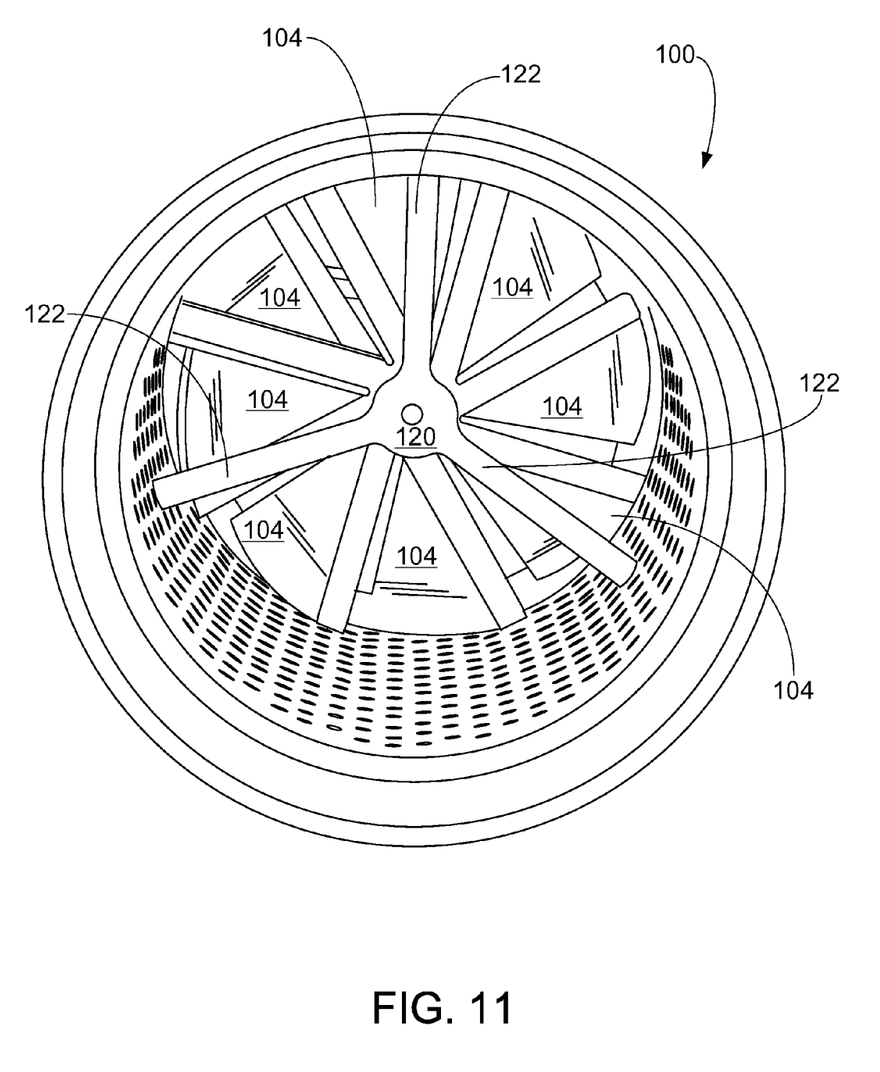
FIG. 11 is a bottom perspective view of the fragrance enhancer of FIG. 9A.
Figure 12:
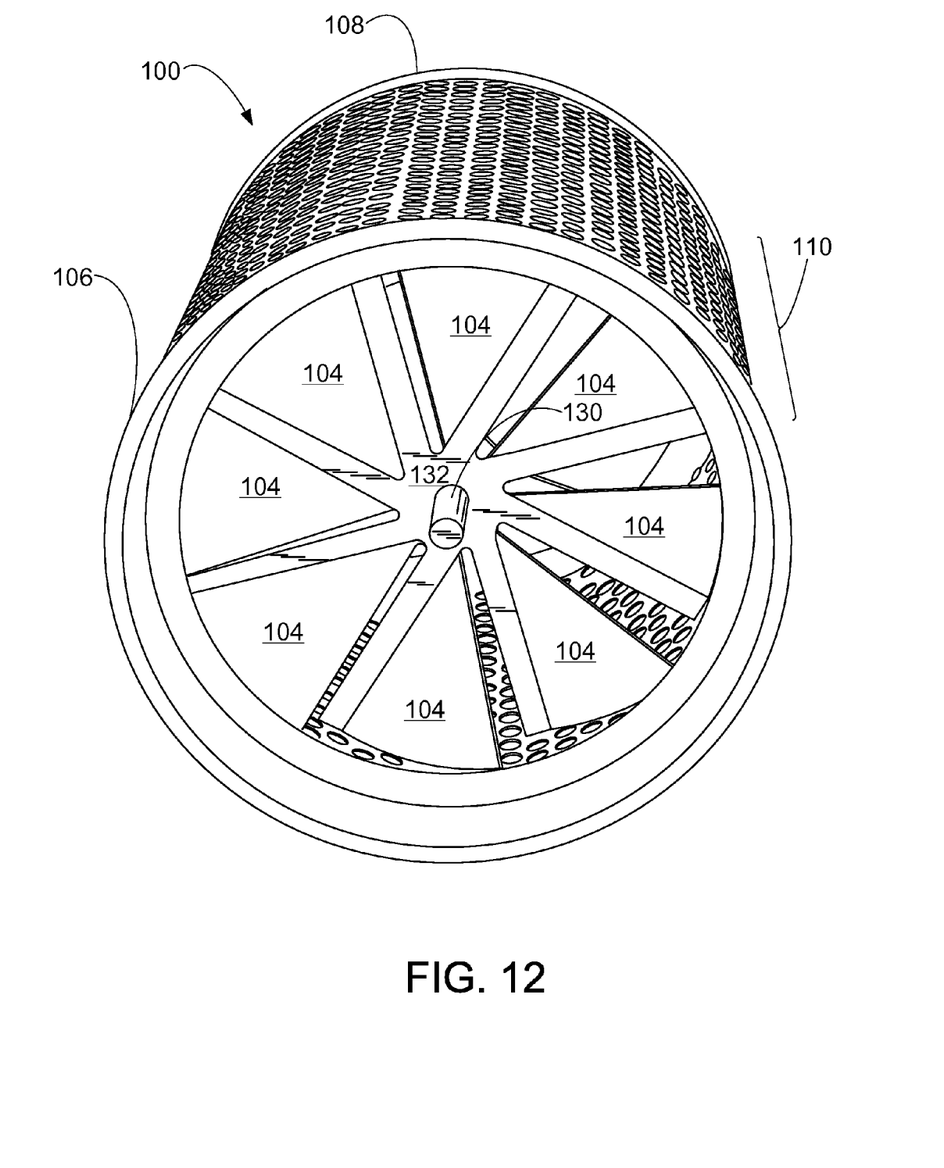
FIG. 12 is a top perspective view of the fragrance enhancer of FIG. 9A.

As can be further seen from FIGS. 9A through 15, fragrance enhancer 100 further includes a fan assembly support bracket 120 designed to permit fan assembly 102 to operatively couple to same. In one embodiment, fan assembly support bracket 120 has three spaced apart arms 122 each having a tooth 122a on the end thereof sized so as to engage at least one opening 124 in cylindrically-shaped perforated screen 110 (more of these arms can also be used). As shown in FIGS. 9A, 11 and 12, the plurality of openings 124 in cylindrically-shaped perforated screen 110 are circular. However, the present invention is not limited thereto. Rather, any desired geometric shape for openings 124 can be utilized including, but not limited to, squares (see FIG. 9B) or triangles (see FIG. 9C).

Figure 13A:
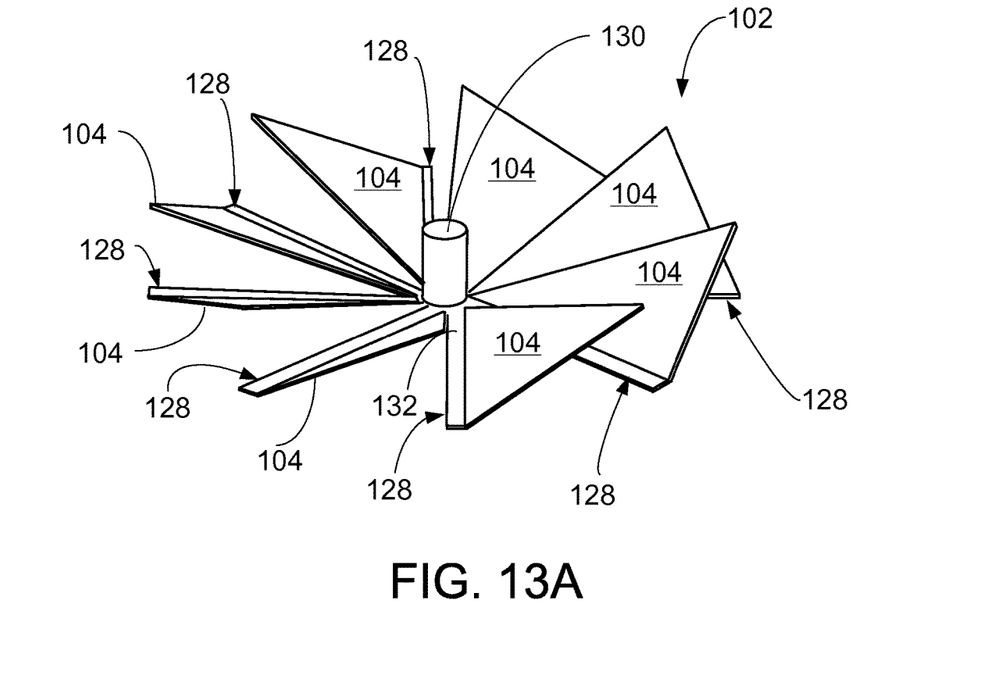
FIG. 13A is a side perspective view of a fan blade assembly in accordance with one embodiment for use in conjunction with the fragrance enhancer of FIG. 9A.
Figure 13B:
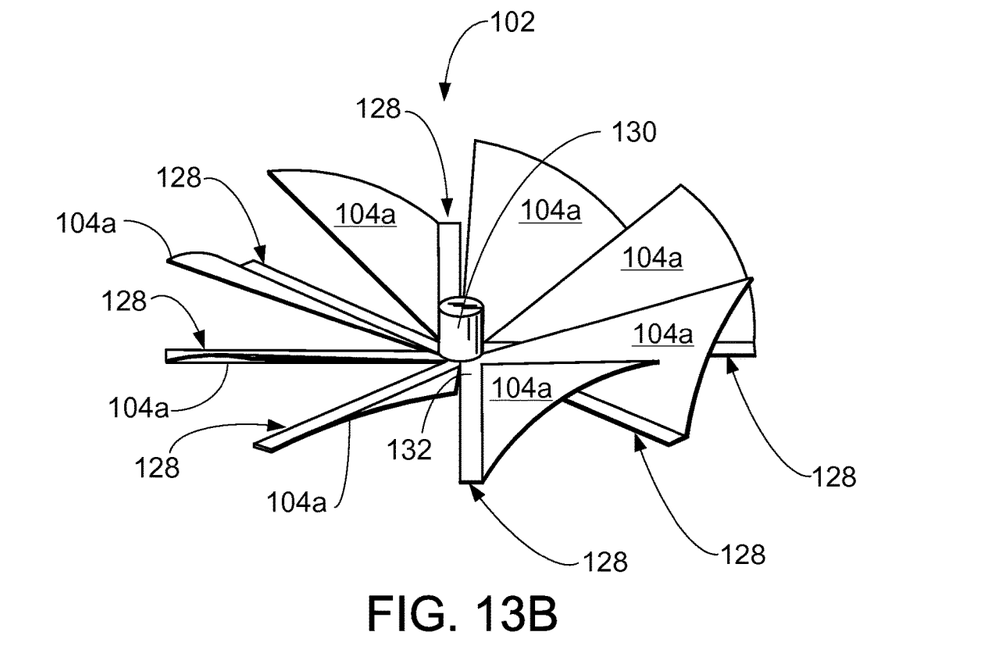
FIG. 13B is a side perspective view of a fan blade assembly in accordance with another embodiment for use in conjunction with the fragrance enhancer of FIG. 9A.
Figure 14:
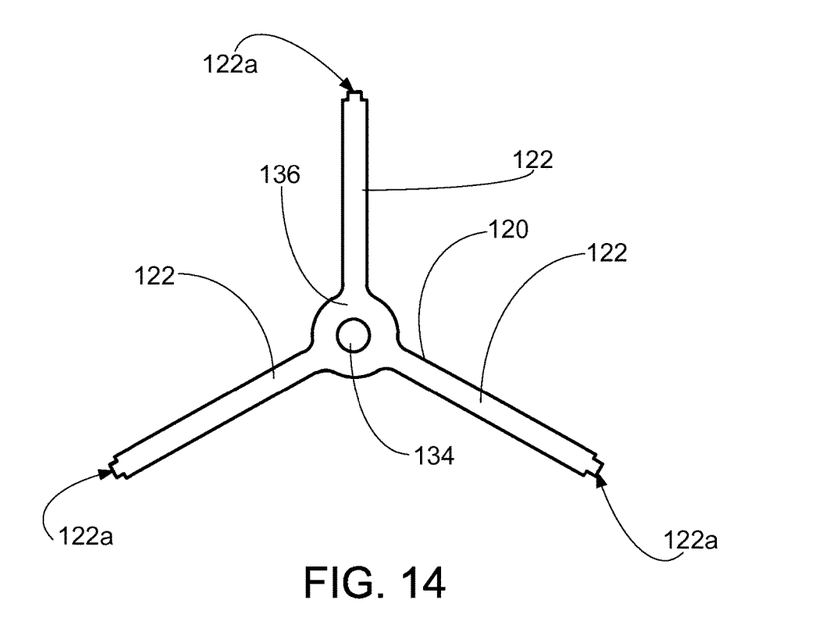
FIG. 14 is a plan view of a fan assembly support bracket in accordance with one embodiment that can be utilized in conjunction with the fragrance enhancer of FIG. 9A.
Figure 15:
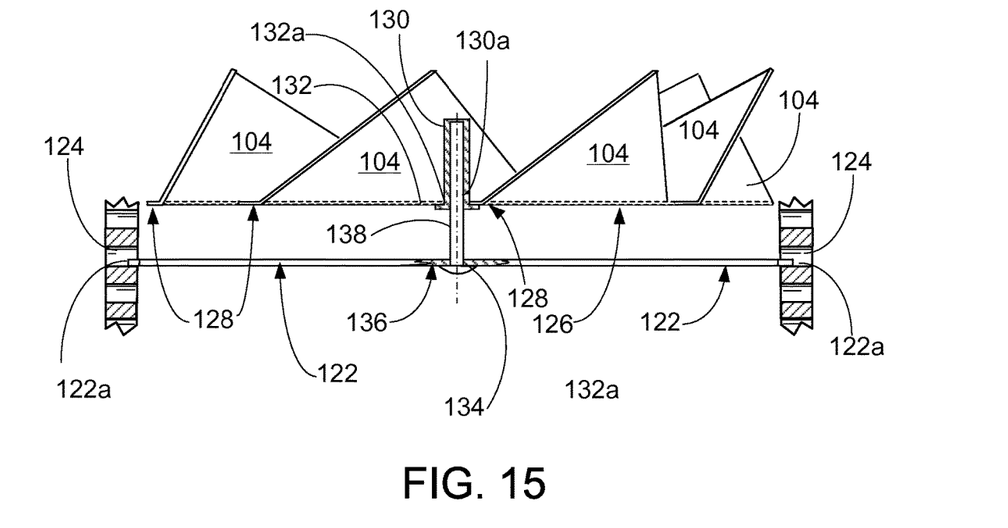
FIG. 15 is a cut-away partial side view of one manner by which the fan assembly of the fragrance enhancer of FIG. 9A is operatively coupled to the fan assembly support bracket of FIG. 14.

As can be seen from FIG. 9A through 15, and in particular FIGS. 13B and 15, blades 104 of fan assembly 102 are both inverted (i.e., meaning blades 104 are formed so that blades 104 are located above an imaginary plane 126 formed by bottom flat edges 128 of each blade 104) and inclined. In another embodiment, as is illustrated in FIG. 13B, fan assembly 102 contains a plurality of blades 104a that are inverted, inclined and have a parabolic arc. As can be seen, fan assembly 102 further includes a post 130 formed in a center hub 132 of fan assembly 102. In one embodiment, post 130 can be integrally formed in fan assembly 102. Alternatively, as is illustrated in FIG. 15, post 130 can be separately formed and inserted from the bottom side of fan assembly 102 through a hole 132a formed in center hub 132. As can further be seen from FIG. 15, post 130 has an opening 130a formed in the underside thereof designed to receive a second upwardly oriented post, or pin, 138 that is operatively inserted through hole 134 formed in center hub 136 of fan assembly support bracket 120. It should be noted that this arrangement for operatively engaging fan assembly 102 with fan assembly support bracket 120 yields a fan that floats freely above the level of fan assembly support bracket 120 and permits fan assembly 102 to rotate freely when heat from candle 142 rises from flame 144 (see FIG. 10). Alternatively other methods known to those of skill in the art can be used to operatively engage fan assembly 102 with fan assembly support bracket 120 including, at a minimum, the other methods described above and/or illustrated with reference to FIGS. 1 through 8B.

It should be noted that all of the various components detailed above of fragrance enhancer 100 are ideally formed from any suitable metal, or metal alloy. Suitable metals, or metal alloys, include, but are not limited to, steel, stainless steel, brass, copper, iron, nickel, aluminum, titanium, etc. It should be noted that individual components of fragrance enhancer 100 can be individually formed from different metals, or metal alloys, or can all be formed from the same metal, or metal alloy. In another embodiment, any portion, or even all of, fragrance enhancer 100 can be formed from any suitable polymer, or plastic material, that is designed to withstand the high temperatures associated with burning candles.

Figure 10:
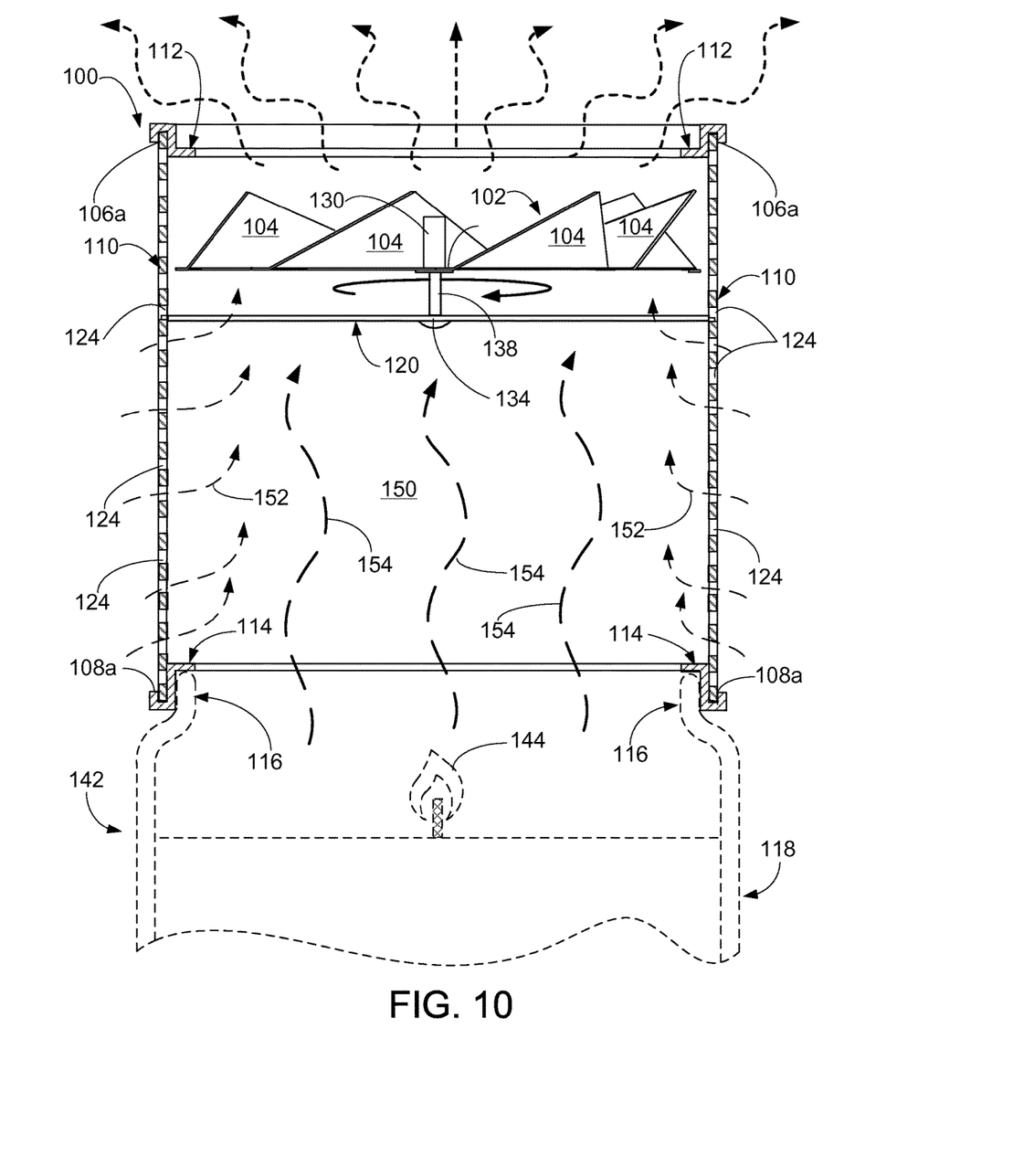
FIG. 10 is a side view of the fragrance enhancer of FIG. 9A.

Regarding the operation of fragrance enhancer 102, fragrance enhancer 102 is advantageous as cylindrically-shaped perforated screen 110 permits the inflow of cool external air into the central cylinder portion 150 thereof where a portion of such air is carried toward the top as detailed by arrows 152 by the convection currents (see arrows 154) caused by the heat rising from candle flame 144 (see FIG. 10). The remaining portion of such incoming air is forced downward toward candle 142 and flame 144 so as to cause candle 142 and flame 144 to burn more efficiently.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A fragrance enhancer for a candle comprising:
   a top cylindrically-shaped ring, wherein the top cylindrically-shaped ring has a top surface and a bottom surface and also has a cylindrical channel formed therein;
   a bottom cylindrically-shaped ring, wherein the bottom cylindrically-shaped ring has a top edge surface a bottom surface and also has a cylindrical channel formed therein;
   a cylindrically-shaped perforated screen, where the cylindrically-shaped perforated screen is designed to operatively engage both of the cylindrical channels located in the top and bottom cylindrically-shaped rings, and wherein the cylindrically-shaped perforated screen extends from the bottom surface of the top cylindrically-shaped ring to the top surface of the bottom cylindrically-shaped ring;
   a fan assembly support bracket formed so as to have a plurality of fan assembly support bracket arms, each fan assembly support bracket arm having a tooth formed at the end thereof so as to operatively engage at least one perforation in the cylindrically-shaped perforated screen; and
   a fan assembly formed from a plurality of inverted inclined fan blades, wherein the fan assembly support bracket and the fan assembly are operatively coupled so that the fan spins in response to rising heat and/or convection currents.

2. The fragrance enhancer of claim 1, wherein the bottom cylindrically-shaped ring has a lip formed therein so as to operatively engage the top portion of a candle.

3. The fragrance enhancer of claim 1, wherein the bottom cylindrically-shaped ring has a lip formed therein.

4. The fragrance enhancer of claim 1, wherein the cylindrically-shaped perforated screen comprises a plurality of circular air inlet holes.

5. The fragrance enhancer of claim 1, wherein the cylindrically-shaped perforated screen comprises a plurality of triangular air inlet holes.

6. The fragrance enhancer of claim 1, wherein the cylindrically-shaped perforated screen comprises a plurality of diamond-shaped air inlet holes.

7. The fragrance enhancer of claim 1, wherein the fan assembly support bracket comprises three spaced apart brackets arms each arm having a tooth its end.

8. The fragrance enhancer of claim 1, wherein each portion thereof is formed from an individually selected metal or metal alloy.

9. The fragrance enhancer of claim 1, wherein each portion thereof is formed from the same metal or metal alloy.

10. The fragrance enhancer of claim 1, wherein each portion thereof is formed from a high temperature resistant plastic or polymer material.

11. A fragrance enhancer for a candle comprising:
    a top cylindrically-shaped ring, wherein the top cylindrically-shaped ring has a cylindrical channel formed therein;
    a bottom cylindrically-shaped ring, wherein the bottom cylindrically-shaped ring has a cylindrical channel formed therein;
    a cylindrically-shaped perforated screen, where the cylindrically-shaped perforated screen is designed to operatively engage both of the cylindrical channels located in the top and bottom cylindrically-shaped rings;
    a fan assembly support bracket formed so as to have a plurality of fan assembly support bracket arms, each fan assembly support bracket arm having a tooth formed at the end thereof so as to operatively engage at least one perforation in the cylindrically-shaped perforated screen; and
    an unpowered fan assembly formed from a plurality of inverted inclined fan blades, wherein the fan assembly support bracket and the unpowered fan assembly are operatively coupled so that the unpowered fan spins in solely response to rising heat and/or convection currents without any reliance on an external force or a power source.

12. The fragrance enhancer of claim 11, wherein the bottom cylindrically-shaped ring has a lip formed therein so as to operatively engage the top portion of a candle.

13. The fragrance enhancer of claim 11, wherein the bottom cylindrically-shaped ring has a lip formed therein.

14. The fragrance enhancer of claim 11, wherein the cylindrically-shaped perforated screen comprises a plurality of circular air inlet holes.

15. The fragrance enhancer of claim 11, wherein the cylindrically-shaped perforated screen comprises a plurality of triangular air inlet holes.

16. The fragrance enhancer of claim 11, wherein the cylindrically-shaped perforated screen comprises a plurality of diamond-shaped air inlet holes.

17. The fragrance enhancer of claim 11, wherein the fan assembly support bracket comprises three spaced apart brackets arms each arm having a tooth its end.

18. The fragrance enhancer of claim 11, wherein each portion thereof is formed from an individually selected metal or metal alloy.

19. The fragrance enhancer of claim 11, wherein each portion thereof is formed from the same metal or metal alloy.

20. The fragrance enhancer of claim 11, wherein each portion thereof is formed from a high temperature resistant plastic or polymer material.

* * * * *